(12) United States Patent
Choi et al.

(10) Patent No.: US 9,146,427 B2
(45) Date of Patent: Sep. 29, 2015

(54) NORBORNENE MONOMER, POLYNORBORNENE DERIVATIVE, LIQUID CRYSTAL PHOTOALIGNMENT FILM CONTAINING THE SAME AND LIQUID CRYSTAL DISPLAY CONTAINING THE SAME

(71) Applicant: LG CHEM, LTD., Seoul (KR)

(72) Inventors: Dai-Seung Choi, Daejeon (KR); Heon Kim, Daejeon (KR); Sung-Ho Chun, Daejeon (KR); Sung-Joon Oh, Daejeon (KR); Dong-Woo Yoo, Daejeon (KR); Yu-Chan Kang, Seoul (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/227,878

(22) Filed: Mar. 27, 2014

(65) Prior Publication Data

US 2014/0213815 A1    Jul. 31, 2014

Related U.S. Application Data

(62) Division of application No. 12/461,590, filed on Aug. 17, 2009, now Pat. No. 8,722,157.

(30) Foreign Application Priority Data

Aug. 18, 2008 (KR) .......................... 10-2008-0080337

(51) Int. Cl.
*C07C 69/76* (2006.01)
*G02F 1/1337* (2006.01)
(Continued)

(52) U.S. Cl.
CPC .......... *G02F 1/13378* (2013.01); *C07C 51/567* (2013.01); *C07C 57/50* (2013.01);
(Continued)

(58) Field of Classification Search
CPC ......... C07C 57/50; C07C 57/56; C08F 32/08; C08F 232/08; C08G 61/06; C08G 61/08
USPC ......... 526/281, 282, 283; 525/55; 560/55, 81; 524/553, 554; 585/360
See application file for complete search history.

(56) References Cited

U.S. PATENT DOCUMENTS

| 5,976,640 A | 11/1999 | Yu et al. |
| 6,201,087 B1 | 3/2001 | Herr et al. |

(Continued)

FOREIGN PATENT DOCUMENTS

| CN | 1592765 A | 3/2005 |
| CN | 1989226 A | 6/2007 |

(Continued)

OTHER PUBLICATIONS

Enholm et al., "Ring-opening metathesis polymerization with [2+2] crosslinking", Aug. 8, 2004, Tetrahedron Letters, V45, p. 8635-8637.*

(Continued)

*Primary Examiner* — Gwendolyn A. Blackwell
*Assistant Examiner* — Ruiyun Zhang
(74) *Attorney, Agent, or Firm* — McKenna Long & Aldridge, LLP

(57) ABSTRACT

The present invention relates to a norbornene monomer, a polynorbornene derivative, a liquid crystal alignment film including the same, and a liquid crystal display device including the same. More particularly, the present invention relates to a norbornene monomer, a polynorbornene derivative, a liquid crystal alignment film including the same, and a liquid crystal display device including the same, which have an alignment property by photoreaction, excellent thermal stability and photoreactivity, the increased photo-reaction rate and reliability of the alignment film, thereby showing high manufacturing process efficiency.

2 Claims, 2 Drawing Sheets

(51) Int. Cl.
*C07C 51/567* (2006.01)
*C07C 69/618* (2006.01)
*C07C 69/734* (2006.01)
*C08F 132/08* (2006.01)
*C07C 57/50* (2006.01)

(52) U.S. Cl.
CPC ............ *C07C 69/618* (2013.01); *C07C 69/734* (2013.01); *C08F 132/08* (2013.01); *G02F 1/133711* (2013.01); *C07C 2102/42* (2013.01); *G02F 1/133788* (2013.01); *Y10T 428/10* (2015.01); *Y10T 428/1005* (2015.01)

(56) References Cited

U.S. PATENT DOCUMENTS

| | | | |
|---|---|---|---|
| 6,218,501 | B1 | 4/2001 | Choi et al. |
| 2006/0159865 | A1 | 7/2006 | Kim et al. |
| 2006/0160970 | A1 | 7/2006 | Kim et al. |
| 2011/0043731 | A1 | 2/2011 | Shin et al. |

FOREIGN PATENT DOCUMENTS

| | | |
|---|---|---|
| JP | 2003-048998 A | 2/2003 |
| KR | 10-2006-0080552 A | 7/2006 |
| KR | 10-0671753 B1 | 7/2006 |
| WO | 2009091225 A2 | 7/2009 |

OTHER PUBLICATIONS

Christian Slugovc et al. The Resting State Makes the Difference: The Influence of the Anchor Group in the ROMP of Norbornene Derivatives. Macromolecular Rapid Communications. 2004, pp. 475-480.

Enholm, Eric et al., "Ring-opening maetathesis polymerization with [2+2]-crosslinking to create new materials", Tetrahedron Letters, vol. 45, 47, pp. 8635-8637, Aug. 8, 2004.

Ahmed Rehab: "Studies of Photoreactive Poly(Norbornene Derivatives) Bearing Chalcome Units", Journal of Macromolecular Science, Part A—Pure and Applied Chemistry, vol. A40, No. 7, pp. 689-703, 2003.

Ichimura et al., "Reversible Change in Alignment Mode of Nematic Liquid Crystals Regulated Photochemically by "Command Surfaces" Modified with an Azobenzene Monolayer", Languir, vol. 4, 1998, pp. 1214-1216.

\* cited by examiner

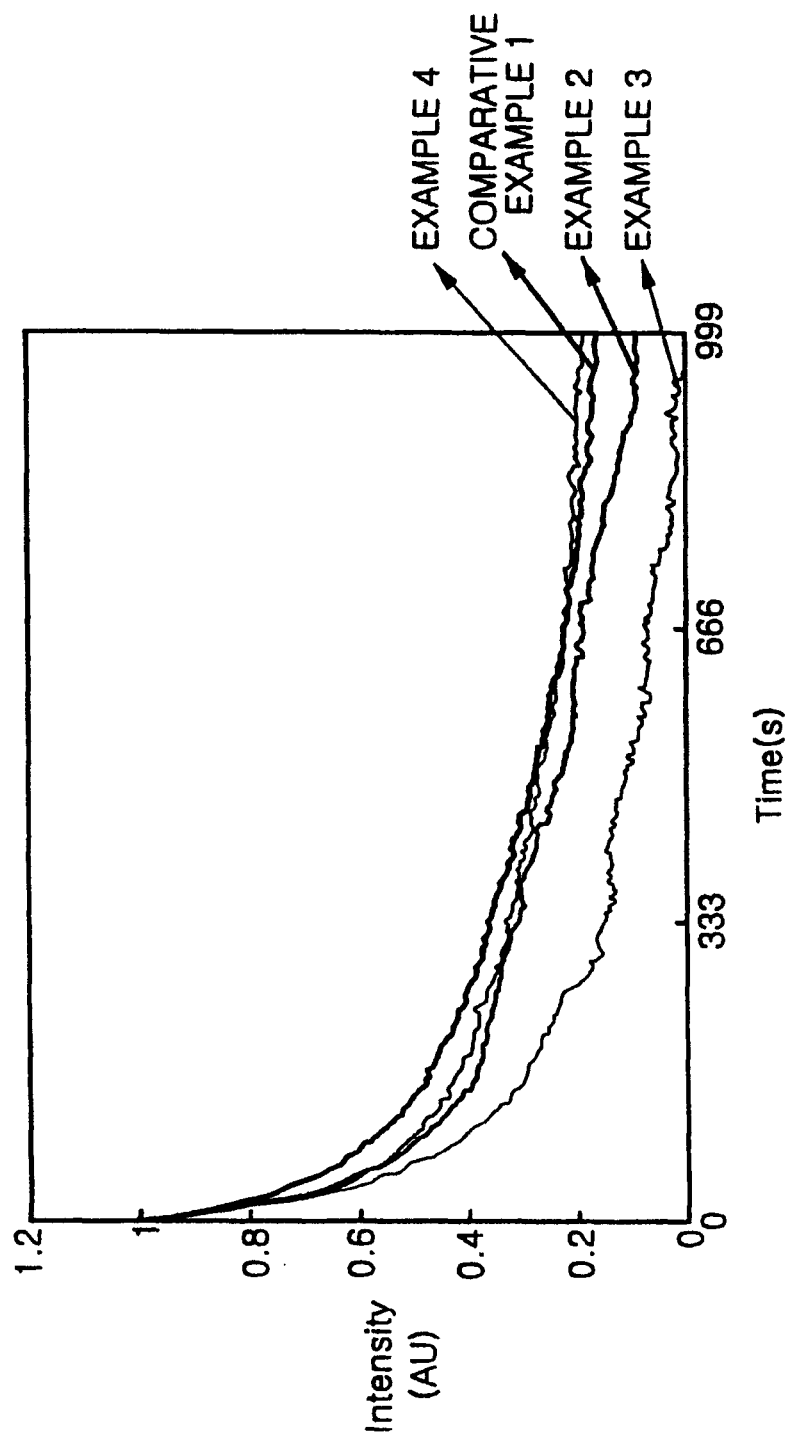

NORBORNENE MONOMER, POLYNORBORNENE DERIVATIVE, LIQUID CRYSTAL PHOTOALIGNMENT FILM CONTAINING THE SAME AND LIQUID CRYSTAL DISPLAY CONTAINING THE SAME

This application is a Divisional of U.S. patent application Ser. No. 12/461,590 filed Aug. 17, 2009, which claims priority to Korean Application No. 10-2008-0080337 filed Aug. 18, 2008, both of which are incorporated by reference for all purposes as if fully set forth herein.

BACKGROUND OF THE INVENTION

1. Field of the Invention

The present invention relates to a material for liquid crystal alignment that is required in alignment of liquid crystal in a process for manufacturing liquid crystal display (LCD). More particularly, the present invention relates to a norbornene monomer, a polynorbornene derivative, a liquid crystal alignment film including the same and a liquid crystal display device including the same.

2. Description of the Related Art

Since a liquid crystal display is light and small as compared to a known Braun tube, the liquid crystal display is used in notebook computers or navigator systems of vehicles. Currently, in accordance with the rapid increase of demand for large monitors, advantages of lightweight and slimness of the liquid crystal display are raised, such that the use of the liquid crystal display in desktop computers is increased.

The most liquid crystal display is a thin film transistor liquid crystal display (TFT-LCD), and light that is emitted from a fluorescent lamp is incident into a liquid crystal panel by reflection and dispersion devices. This light may be blocked by a liquid crystal layer in which birefringence is changed by voltage controlled by the thin film transistor (TFT) or may pass through them.

The liquid crystal panel forms a lower substrate of a cell by layering a thin film transistor driving device and an ITO (Indium-Tin-Oxide) transparent electrode on a glass substrate and then layering the alignment film. On the internal surfaces of a pair of upper and lower substrates, a spacer is formed by a sealant in order to inject the liquid crystal material therebetween, a polarizing film is attached to the external surfaces of the glass substrates, and finally, the liquid crystal material is injected between a pair of substrates and cured to manufacture the liquid crystal display cell.

In this TFT-LCD, in order to use the liquid crystal as an optical switch, it is required that the liquid crystal disposed on the layer on which the thin film transistor is formed at the innermost portion of the display cell is initially aligned in a predetermined direction. In order to implement this, the liquid crystal alignment film is used.

As the method for aligning the liquid crystal, currently, in most thin film transistor liquid crystal displays, a rubbing method in which liquid crystal is aligned by physically contacting a substrate on which a polymer is coated using soft cotton or nylon velvet is widely used.

However, the alignment of the liquid crystal by the rubbing has problems in that the thin film transistor may be broken or cross track short may occur because of the electrostatics generated by the rubbing, and defects may be increased by attracting circumferential dust.

Accordingly, in order to solve the problems of the rubbing method, the non-contact type of liquid crystal alignment methods are studied, and the method having the highest possibility among them is an alignment method for manufacturing a liquid crystal alignment film by using light irradiation.

The possibility of the light alignment method was found by using an azobenzene compound (K. Ichimura et al., Langmuir, 4, 1214, 1988). Thereafter, various kinds of polymer compounds such as polymaleimide (H. J. Choi et al., U.S. Pat. No. 6,218,501), polyolefine (R. H. Herr et al., U.S. Pat. No. 6,201,087) and the like have been developed as a photoalignment material.

Among them, in the case of polymer that includes the cinnamate-based photoreactive group at a side chain thereof, the anisotropic property is formed by the cyclobutane ring that is formed through the [2+2] cycloaddition reaction, such that the excellent liquid crystal alignment can be obtained. However, in general, since the photoreactivity is low and the thermal stability is poor, the direction of generated cyclobutane is little changed, and thus the anisotropic property is changed. Accordingly, there is a problem in that the reliabilities of the alignment film and the liquid crystal display device that adopts the alignment film are lowered.

SUMMARY OF THE INVENTION

It is an object of the present invention to provide a norbornene monomer, a polynorbornene derivative, a liquid crystal alignment film including the same, and a liquid crystal display device including the same, which have excellent thermal stability, high photoreactivity, the increased photo-reaction rate and reliability of the alignment film, thereby showing high manufacturing process efficiency.

The present invention provides a norbornene monomer that is represented by the following Formula 1:

[Formula 1]

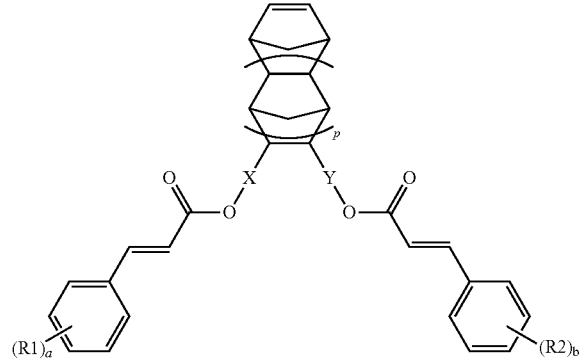

wherein P is an integer in the range of 0 to 4,

X and Y are the same as each other or different from each other, and substituted or unsubstituted $C_{1-20}$ alkylene, carbonyl, carboxy and substituted or unsubstituted $C_{6-40}$ arylene, a and b are an integer in the range of 0 to 5, R1 and R2 are the same as each other or different from each other, and each selected from the group consisting of substituted or unsubstituted $C_{1-20}$ alkyl, substituted or unsubstituted $C_{1-20}$ alkoxy, substituted or unsubstituted $C_{6-30}$ aryloxy, substituted or unsubstituted $C_{6-40}$ aryl, substituted or unsubstituted $C_{6-40}$ alkoxyaryl and halogen groups.

In addition, the present invention provides a method for manufacturing a norbornene monomer, which comprises the steps of a) manufacturing exo-Nadic anhydride by thermally rearranging endo-nadic anhydride; b) reducing the manufactured exo-nadic anhydride by using a reducing agent; c) esterifying the product that is manufactured in step b) and an acidic cinnamate derivative.

The present invention provides a norbornene monomer that is represented by the following Formula 1:

[Formula 1]

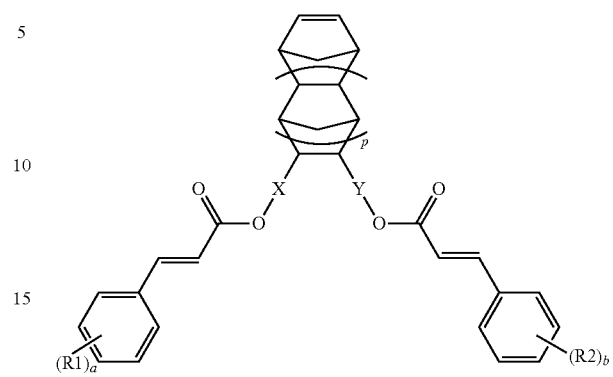

wherein P is an integer in the range of 0 to 4,

X and Y are the same as each other or different from each other, and substituted or unsubstituted $C_{1-20}$ alkylene, carbonyl, carboxy and substituted or unsubstituted $C_{6-40}$ arylene, a and b are an integer in the range of 0 to 5, R1 and R2 are the same as each other or different from each other, and each selected from the group consisting of substituted or unsubstituted $C_{1-20}$ alkyl, substituted or unsubstituted $C_{1-20}$ alkoxy, substituted or unsubstituted $C_{6-30}$ aryloxy, substituted or unsubstituted $C_{6-40}$ aryl, substituted or unsubstituted $C_{6-40}$ alkoxyaryl and halogen groups.

The norbornene monomer that is represented by Formula 1 can be manufactured through the steps of a) manufacturing exo-nadic anhydride by thermally rearranging endo-nadic anhydride; b) reducing the manufactured exo-nadic anhydride by using a reducing agent; and c) esterifying the manufactured product and an acidic cinnamate derivative.

In step a), in the case of when the exo-nadic anhydride that is manufactured by thermally rearranging the endo-nadic anhydride is used, more excellent yield is obtained as compared to the case of when it is manufactured by using the monomer that includes only the endo-nadic anhydride.

It is preferable that the thermal rearranging temperature is in the range of 180 to 260° C. In the case of when the thermal rearrangement temperature is less than 180° C., the yield may become very low, and in the case of when the thermal rearrangement temperature is more than 260° C., since the endo-nadic anhydride is decomposed, the rearrangement may not occur.

The reducing agent that is used in step b) may be $LiAlH_4$, $NaBH_4$ or DIBAL (diisobutylaluminium hydride), but is not limited thereto.

In step c), the esterification may use a method for using a coupling agent such as DCC (dicyclohexyl carbodiimide) or EDC (1-ethyl-3-(3-dimethylaminopropyl)carbodiimide) or a Dean-Stark distillation method using a catalyst such as $Zr(OAc)_x(OH)_y$, but is not limited thereto. Herein, x and y have a correlation of x+y=4.

The norbornene monomer that is represented by Formula 1 has two cinnamate groups and cannot be manufactured by using a known method, but in the present invention, the norbornene monomer that is represented by Formula 1 can be manufactured by using the above method.

In addition, the present invention provides a polynorbornene derivative including a repeating unit that is represented by the following Formula 2:

[Formula 2]

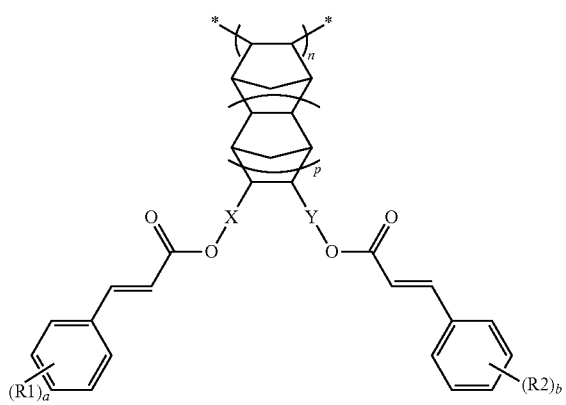

wherein P is an integer in the range of 0 to 4,

X and Y are the same as each other or different from each other, and substituted or unsubstituted $C_{1-20}$ alkylene, carbonyl, carboxy and substituted or unsubstituted $C_{6-40}$ arylene, n is an integer in the range of 50 to 5,000, a and b are an integer in the range of 0 to 5, R1 and R2 are the same as each other or different from each other, and each selected from the group consisting of substituted or unsubstituted $C_{1-20}$ alkyl, substituted or unsubstituted $C_{1-20}$ alkoxy, substituted or unsubstituted $C_{6-30}$ aryloxy, substituted or unsubstituted $C_{6-40}$ aryl, substituted or unsubstituted $C_{6-40}$ alkoxyaryl and halogen groups.

In addition, the present invention provides a liquid crystal alignment film which comprises the polynorbornene derivative.

In addition, the present invention provides a method for manufacturing a liquid crystal alignment film, which comprises the steps of 1) dissolving the polynorbornene derivative in an organic solvent, and coating the dissolved derivative on a surface of a substrate, such that a coat is formed; 2) drying the solvent that is included in the coat; and 3) irradiating polarized ultraviolet rays onto the surface of the dried coat in order to carry out the alignment treatment.

In addition, the present invention provides a liquid crystal display device which comprises the liquid crystal alignment film.

The liquid crystal alignment film that includes the polynorbornene derivative according to the present invention has an alignment property by photoreaction, excellent thermal stability, high photoreactivity, the increased photo-reaction rate and reliability of the alignment film, thereby showing high manufacturing process efficiency.

BRIEF DESCRIPTION OF THE DRAWINGS

FIG. 2 is a graph that illustrates Fourier Transform Infrared Spectrophotometer (FT-IR) spectra of Examples 1, 2, and 4 and Comparative Example 1 according to the present invention.

DETAILED DESCRIPTION OF THE PREFERRED EMBODIMENTS

Figure 1:
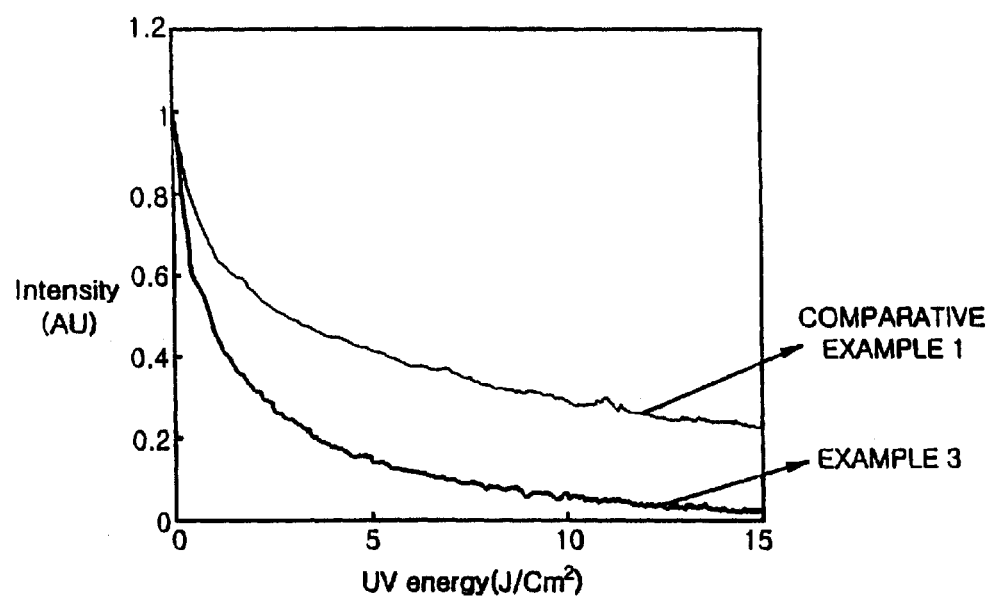
FIG. 1 is a graph that illustrates Fourier Transform Infrared Spectrophotometer (FT-IR) spectra of Example 3 and Comparative Example 1 according to the present invention.

Hereinafter, the present invention will be described in detail.

[Formula 2]

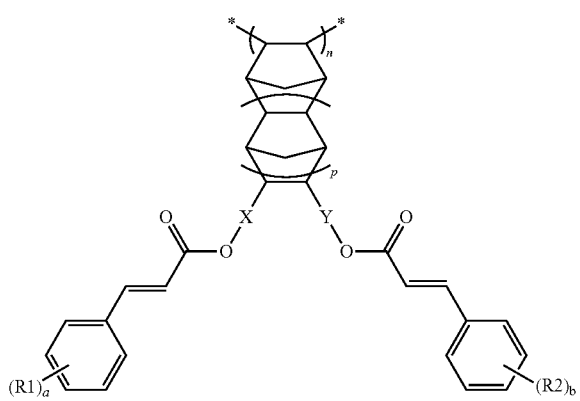

wherein P is an integer in the range of 0 to 4,

X and Y are the same as each other or different from each other, and substituted or unsubstituted $C_{1-20}$ alkylene, carbonyl, carboxy and substituted or unsubstituted $C_{6-40}$ arylene, n is an integer in the range of 50 to 5,000, a and b are an integer in the range of 0 to 5, and R1 and R2 are the same as each other or different from each other, and each selected from the group consisting of substituted or unsubstituted $C_{1-20}$ alkyl, substituted or unsubstituted $C_{1-20}$ alkoxy, substituted or unsubstituted $C_{6-30}$ aryloxy, substituted or unsubstituted $C_{6-40}$ aryl, substituted or unsubstituted $C_{6-40}$ alkoxyaryl and halogen groups.

The polynorbornene derivative that includes the repeating unit that is represented by Formula 2 can be manufactured by polymerizing the norbornene monomer derivative that is represented by Formula 1 under a Group X catalyst, for example, a Pd-based catalyst.

It is preferable that the number-average molecular weight (Mn) the polynorbornene derivative that includes the repeating unit that is represented by Formula 2 is 10,000 to 2,000,000.

Examples of the arylene include phenylene, naphthalene, biphenylene, anthrylene or etc.

Examples of the halogen groups include fluorine, chlorine, bromine, iodine or etc.

The polynorbornene derivative that includes the repeating unit of Formula 2 may include any one of repeating units that are represented by the following Formula 3 to Formula 6, but is not limited thereto.

[Formula 3]

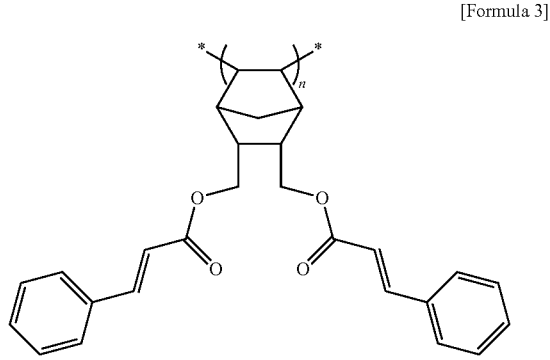

wherein n is an integer in the range of 50 to 5,000,

[Formula 4]

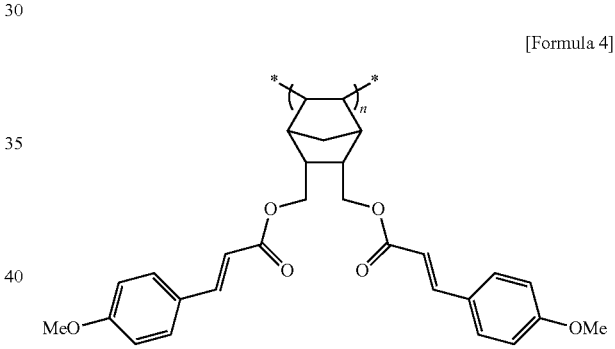

wherein n is an integer in the range of 50 to 5,000,

[Formula 5]

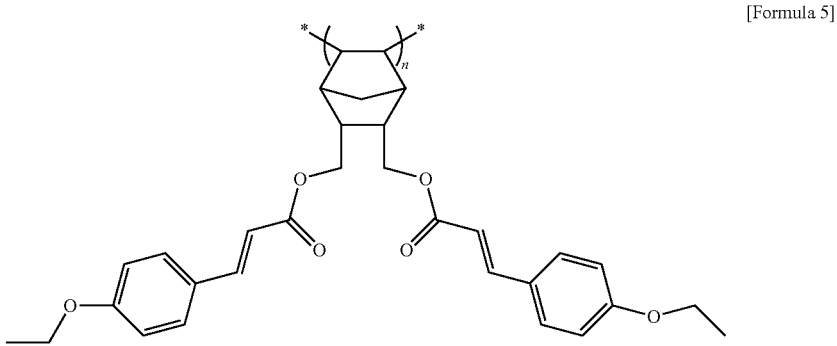

wherein n is an integer in the range of 50 to 5,000,

[Formula 6]

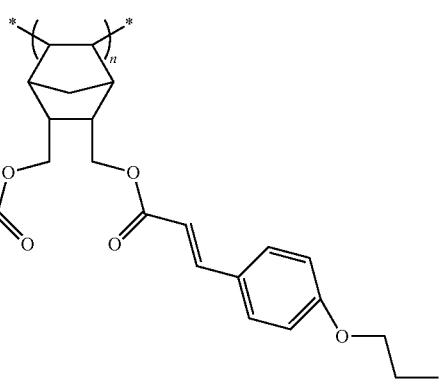

wherein n is an integer in the range of 50 to 5,000.

In the above compound, as the alkyl group of the alkoxy group that is attached to an end of phenyling becomes longer, the pretilt angle of the liquid crystal molecule is improved. In detail, it is preferable that $C_{1-20}$ alkyl group is used.

In addition, the present invention provides a liquid crystal alignment film that includes the polynorbornene derivative including the repeating unit that is represented by Formula 2.

The method for manufacturing a liquid crystal alignment film according to the present invention comprises the steps of 1) dissolving the polynorbornene derivative in an organic solvent, and coating the dissolved derivative on a surface of a substrate, such that a coat is formed; 2) drying the solvent that is included in the coat; and 3) irradiating polarized ultraviolet rays onto the surface of the dried coat in order to carry out the alignment treatment.

In step 1), the concentration of the solution, the kind of the solvent, and the coating method can be determined according to the kind of the polynorbornene derivative and the purpose thereof.

In step 1), as the organic solvent, there are cyclopentanone, cyclohexanone, N-methylpyrrolidone, DMF (Dimethyl formamide), THF (Tetrahydrofuran), $CCl_4$ or a mixture thereof, but it is not limited thereto.

In addition, in order to ensure the uniformity of the film thickness of the coat and prevent printing defects after the coating treatment, the solvent such as ethylene glycol monoethyl ether acetate, ethylene glycol monoisopropyl ether, ethylene glycol monomethyl ether may be used in conjunction with the above organic solvent.

In step 1), the solution may be coated on the surface of the substrate on which a transparent conductive film or a metal electrode is patterned by using a method such as a roll coater method, a spinner method, a printing method, an inkjet spraying method, a slit nozzle method and the like.

In addition, while the solution is coated, in order to more improve the attachment property of the substrate surface, the transparent conductive film, the metal electrode, and the coat, a compound including a functional silane, a compound including a functional fluoro, and a compound including a functional titanium may be previously coated on the substrate.

In step 1), the temperature when the polynorbornene derivative is dissolved in the solution is in the range of 0 to 100° C. and more preferably 15 to 70° C.

The concentration of the solid of the polynorbornene derivative is selected in consideration of the molecular weight, the viscosity, the volatility, and the like of the polynorbornene derivative that is represented by Formula 2, and in order to achieve the desired liquid crystal alignment effect and ensure an appropriate viscosity so as to have a preferable coating property, it is preferable that it is selected in a range of 0.5 to 20 wt % on the basis of the total weight of the solution in which the polynorbornene derivative is dissolved in the organic solvent.

In step 2), the solvent may be dried by heating the coat or using a vacuum evaporation method and the like.

When the solvent in step 2) is dried, it may be dried at a temperature in the range of 35 to 80° C. and preferably 50 to 75° C. within 1 hour.

In step 3), the alignment treatment can be carried out by irradiating ultraviolet rays at a wavelength range of 150 to 450 nm onto the surface of the coat that is dried in step 2). At this time, the intensity of light used in exposure is different according to the kind of the polynorbornene derivative, and energy in the range of 50 $mJ/cm^2$ to 10 $J/cm^2$, and preferably 500 $mJ/cm^2$ to 5 $J/cm^2$ may be irradiated.

The alignment treatment is carried out by irradiating the polarized ultraviolet rays selected from ultraviolet rays that are subjected to the polarizing treatment by using a method in which ultraviolet rays are penetrated through or reflected by ① a polarizing device using a substrate in which a dielectric anisotropic material is coated on the surface of the transparent substrate such as quartz glass, sodalime glass, sodalime-free glass and the like, ② a polarizing plate on which aluminium or metal wire is finely deposited, or ② a Bruster polarizing device using reflection by quartz glass. At this time, the polarized ultraviolet rays may be irradiated in a direction that is vertical to the surface of the substrate, or may be irradiated at a predetermined incident angle. In this way, the alignment ability of the liquid crystal molecules is provided to the coat.

It is preferable that the substrate temperature when ultraviolet rays are irradiated in step 3) is normal temperature. However, according to circumstances, ultraviolet rays may be irradiated while ultraviolet rays are heated in a temperature range of 80° C. or less.

It is preferable that the film thickness of the final coat that is formed by using the above process is in the range of 0.002 to 2 μm, and it is more preferable that the film thickness is in the range of 0.004 to 0.6 μm in order to be desirably used in the display device.

After it is subjected to the above process, the liquid crystal alignment film that has the liquid crystal alignment ability that is stable in respects to external heat, and physical and chemical impact can be obtained.

The liquid crystal alignment film according to the present invention may include a general solvent or additive that is known in the art in addition to the polynorbornene derivative.

In addition, the present invention provides a liquid crystal display that includes the liquid crystal alignment film.

The liquid crystal display can be manufactured according to a general method that is known in the art. An example thereof will be described. After a photoreactive adhesive that includes a ball spacer is coated on ends of any one glass substrate of two glass substrates which have the liquid crystal alignment film and in which a photoreaction is induced according to the present invention, the other glass substrate is attached to it, ultraviolet rays are irradiated on the portion on which the adhesive is coated, and the cell is attached thereto. Next, after the liquid crystal is injected into the manufactured cell and is subjected to the heat treatment, the liquid crystal cell is finally manufactured.

In the following Examples, all operations for treating compounds that were sensitive air or water were carried out by using the standard Schlenk technique or the dry box technique. The nuclear magnetic resonance (NMR) spectrum was obtained by using the Bruker 300 spectrometer, and at this time, $^1$H NMR was measured at 300 MHz and $^{13}$C NMR was measured at 75 MHz, respectively. The molecular weight and the molecular weight distribution of the polymer were measured by using GPC (gel permeation chromatography), and at this time, the polystyrene sample was used as the standard.

Toluene was purified by distilling it in potassium/benzophenone, and dichloromethane was distilled and purified in $CaH_2$.

EXAMPLE

Synthetic Example 1

Thermal Rearrangement of Nadic Anhydride

Nadic anhydride (ACROS, 225 g, 1.4 mol, pure endo isomer) was put into the 500 ml 2-neck round bottom flask, and refluxed while the temperature was increased to 180° C. Next, while it was agitated at 300 rpm, it was reacted for 6 hours, the reactants were cooled and recrystallized with benzene. The product that was rearranged by 80% exo isomers were obtained by carrying out the recrystallization twice (yield: 40%).

The NMR analysis results of the pure endo isomer compound are described below.

$^1$H-NMR (300 MHz, CDCl$_3$): δ6.31 (2H), 3.50 (2H), 3.59 (2H), δ1.57 to 1.80 (2H)

In addition, the results of the NMR analysis that was carried out in order to confirm that the 80% exo isomer nadic anhydride compound that was manufactured through thermal rearrangement was formed are described below.

$^1$H-NMR (300 MHz, CDCl$_3$): δ6.30 to 6.34 (2H), 3.44 (2H) 3.01 (2H), δ1.68 (1H), 61.42 (1H)

Synthetic Example 2

Synthesis of 5-norbornene-2,3-di(methanol)

The exo isomer nadic anhydride (37 g, and 0.22 mol) that was manufactured in Synthetic Example 1, and 500 ml of THF were put into the 1 L two-neck flask, and agitated in the ice-water bath at 0° C. Lithium aluminium hydride (LiAlH$_4$) (Aldrich, 7.2 g, 0.19 mol) was dissolved in 200 ml of THF, and slowly put into the reactants by using the additional flask. After 1 hour, the reactants were additionally agitated at normal temperature for 3 hours. The reactant solution was diluted with ethyl acetate, moved into the separatory funnel, washed with water and NaHCO$_3$ several times, and distilled under reduced pressure to remove the solvent. The pure product was obtained by purifying the product by using the column chromatography (eluent where the ratio of n-Hexane: Ethxyl acetate is 1:1) (yield: 38%).

In addition, the results of the NMR analysis that was carried out in order to confirm that the compound that was manufactured by using the above process was formed are described below.

$^1$H-NMR (300 MHz, CDCl$_3$): δ6.2 (2H), 4.12 to 4.24 (2H), 3.76 (4H), 3.62 (1H), 3.37 (1H), 2.20 (1H), 1.80 (1H), 1.38 to 1.42 (1H), 1.24 to 1.26 (1H)

Synthetic Example 3-(1)

Synthesis of 5-norbornene-2,3-di(cinnamate)

5-norbornene-2,3-di(methanol) (15.4 g, and 0.1 mol) that was manufactured in Synthetic Example 2, the cinnamic acid (Aldrich, 32.6 g, 0.22 mol), dicyclohexyl carbodiimide (DCC: Aldrich, 45.4 g, 0.22 mol) and 4-dimethyl aminopyridine (DMAP: Aldrich, 2.4 g, 0.02 mol) were put into the 250 ml two-neck flask, and dissolved in 500 ml of MC. After the temperature was lowered to 0° C., they were reacted for 1 hour, and reacted at normal temperature for overnight. After the reaction was finished, the manufactured urea (nondissolved white solid) was filtered and the solvent of the filtered solution was removed. The obtained product was extracted with a great amount of ethyl acetate, washed with the NaHCO$_3$ aqueous solution, dried with anhydrous MgSO$_4$, and filtered. In addition, the yellow oil type product was obtained by removing the solvent by using the rotary evaporator. Next, 5-norbornene-2,3-dicinnamate that was the pure product was obtained by carrying out the recrystallization and the purification by using acetonitrile (yield: 30%).

Synthetic Example 3-(2)

Synthesis of 5-norbornene-2,3-di(cinnamate)

5-norbornene-2,3-di(methanol) (15.4 g, and 0.1 mol) that was manufactured in Synthetic Example 2, the cinnamic acid (Aldrich, 32.6 g, 0.22 mol), and Zr(OAc)$_x$(OH)$_y$ (x+y=4) (Aldrich, 243 mg, 1 mmol) were put into the 250 ml two-neck flask, and dissolved in 500 ml of toluene. After the Dean-Stark distillation device was installed, the temperature was increased to 130° C., and the reflux was carried out. After the reaction was carried out for 24 hours, they were washed with 10% HCl aqueous solution, and extracted with a great amount of ethyl acetate. The obtained product was washed with the NaHCO$_3$ aqueous solution, dried with anhydrous MgSO$_4$, and filtered. In addition, the yellow oil type product was obtained by removing the solvent by using the rotary evaporator. Next, 5-norbornene-2,3-dicinnamate that was the pure product was obtained by carrying out the recrystallization and the purification by using acetonitrile (yield: 50%). The results of the NMR analysis that was carried out in order to confirm that the compound that was manufactured by using the above process was formed are described below.

$^1$H-NMR (300 MHz, CDCl$_3$): δ7.72 to 7.67 (2H), 7.50 to 7.53 (4H), 7.38 to 7.35 (6H), 6.42 to 6.48 (2H), 6.23 to 6.34 (2H), 3.95 to 4.12 (4H), 3.0 (2H), 2.67 to 2.69 (2H), 1.39 to 1.59 (2H)

Synthetic Example 4-(1)

Synthesis of 5-norbornene-2,3-di(4-methoxy cinnamate)

5-norbornene-2,3-di(methanol) (15.4 g, and 0.1 mol) that was manufactured in Synthetic Example 2,4-methoxy cinnamic acid (Aldrich, 39.2 g, 0.22 mol), dicyclohexyl carbodiimide (DCC: Aldrich, 45.4 g, 0.22 mol) and 4-dimethyl aminopyridine (DMAP: Aldrich, 2.4 g, 0.02 mol) were put into the 250 ml two-neck flask, and dissolved in 500 ml of MC. After the temperature was lowered to 0° C., they were reacted for 1 hour, and reacted at normal temperature for overnight. After the reaction was finished, the manufactured urea (nondissolved white solid) was filtered and the solvent of the filtered solution was removed. The obtained product was extracted with a great amount of ethyl acetate, washed with the $NaHCO_3$ aqueous solution, dried with anhydrous $MgSO_4$, and filtered. In addition, the yellow oil type product was obtained by removing the solvent by using the rotary evaporator. Next, 5-norbornene-2,3-dimethoxy cinnamate that was the pure product was obtained by carrying out the recrystallization and the purification by using MC (yield: 10%).

Synthetic Example 4-(2)

Synthesis of 5-norbornene-2,3-di(4-methoxy cinnamate)

5-norbornene-2,3-di(methanol) (15.4 g, and 0.1 mol) that was manufactured in Synthetic Example 2, the 4-methoxy cinnamic acid (Aldrich, 39.2 g, 0.22 mol), and $Zr(OAc)_x(OH)_y$ (x+y=4) (Aldrich, 243 mg, 1 mmol) were put into the 250 ml two-neck flask, and dissolved in 500 ml of toluene. After the Dean-Stark distillation device was installed, the temperature was increased to 130° C., and the reflux was carried out. After the reaction was carried out for 48 hours, they were washed with 10% HCl aqueous solution, and extracted with a great amount of ethyl acetate. The obtained product was washed with the $NaHCO_3$ aqueous solution, dried with anhydrous $MgSO_4$, and filtered. In addition, the yellow oil type product was obtained by removing the solvent by using the rotary evaporator. Next, 5-norbornene-2,3-dimethoxy cinnamate that was the pure product was obtained by carrying out the recrystallization and the purification by using MC (yield: 35%).

The results of the NMR analysis that was carried out in order to confirm that the compound that was manufactured by using the above process was formed are described below.

$^1$H-NMR (300 MHz, $CDCl_3$): δ7.59 to 7.78 (2H), 7.42 to 7.51 (4H), 6.84 to 6.91 (4H), 6.26 to 6.38 (2H), 6.15 to 6.18 (2H), 4.12 to 4.36 (2H), 3.81 to 3.83 (6H), 3.61 to 3.31 (2H), 2.51 to 2.95 (2H), 1.75 to 1.91 (2H), 1.22 to 1.52 (2H)

Synthetic Example 5-(1)

Synthesis of 5-norbornene-2,3-di(4-ethoxy cinnamate)

5-norbornene-2,3-di(methanol) (15.4 g, and 0.1 mol) that was manufactured in Synthetic Example 2,4-ethoxy cinnamic acid (42.3 g, 0.22 mol), dicyclohexyl carbodiimide (DCC: Aldrich, 45.4 g, 0.22 mol) and 4-dimethyl aminopyridine (DMAP: Aldrich, 2.4 g, 0.02 mol) were put into the 250 ml two-neck flask, and dissolved in 500 ml of MC. After the temperature was lowered to 0° C., they were reacted for 1 hour, and reacted at normal temperature for overnight. After the reaction was finished, the manufactured urea (nondissolved white solid) was filtered and the solvent of the filtered solution was removed. The obtained product was extracted with a great amount of ethyl acetate, washed with the $NaHCO_3$ aqueous solution, dried with anhydrous $MgSO_4$, and filtered. In addition, the product was obtained by removing the solvent by using the rotary evaporator. The pure product was obtained by purifying it by using the column chromatography (n-hexane:ethyl acetate=4:1) and recrystallizing it with n-hexane again (yield: 63%).

Synthetic Example 5-(2)

Synthesis of 5-norbornene-2,3-di(4-ethoxy cinnamate)

5-norbornene-2,3-di(methanol) (15.4 g, and 0.1 mol) that was manufactured in Synthetic Example 2, the 4-ethoxy cinnamic acid (42.3 g, 0.22 mol), and $Zr(OAc)_x(OH)_y$ (x+y=4) (Aldrich, 243 mg, 1 mmol) were put into the 250 ml two-neck flask, and dissolved in 500 ml of toluene. After the Dean-Stark distillation device was installed, the temperature was increased to 130° C., and the reflux was carried out. After the reaction was carried out for 48 hours, they were washed with 10% HCl aqueous solution, and extracted with a great amount of ethyl acetate. The obtained product was washed with the $NaHCO_3$ aqueous solution, dried with anhydrous $MgSO_4$, and filtered. In addition, the product was obtained by removing the solvent by using the rotary evaporator. The pure product was obtained by purifying it by using the column chromatography (n-hexane:ethyl acetate=4:1) and recrystallizing it with n-hexane again (yield: 63%).

The results of the NMR analysis that was carried out in order to confirm that the compound that was manufactured by using the above process was formed are described below.

$^1$H-NMR (300 MHz, $CDCl_3$): δ7.61 to 7.67 (2H), 7.40 to 7.47 (4H), 6.84 to 6.88 (4H), 6.29 to 6.34 (2H), 6.20 to 6.22 (2H), 4.38 to 4.41 (2H), 4.19 to 4.23 (2H), 4.03 to 4.07 (4H), 2.62 to 2.98 (2H), 1.58 to 2.00 (4H) 1.40 to 1.43 (6H)

Synthetic Example 6-(1)

Synthesis of 5-norbornene-2,3-di(4-propoxy cinnamate)

5-norbornene-2,3-di(methanol) (15.4 g, and 0.1 mol) that was manufactured in Synthetic Example 2,4-propoxy cinnamic acid (45 g, 0.22 mol), dicyclohexyl carbodiimide (DCC: Aldrich, 45.4 g, 0.22 mol) and 4-dimethyl aminopyridine (DMAP: Aldrich, 2.4 g, 0.02 mol) were put into the 250 ml two-neck flask, and dissolved in 500 ml of MC. After they were reacted for 1 hour at 0° C., and reacted at normal temperature for overnight. After the reaction was finished, the manufactured urea (nondissolved white solid) was filtered and the solvent of the filtered solution was removed. The obtained product was extracted with a great amount of ethyl acetate, washed with the $NaHCO_3$ aqueous solution, dried with anhydrous $MgSO_4$, and filtered. In addition, the product was obtained by removing the solvent by using the rotary evaporator. The pure product was obtained by purifying it by using the column chromatography (n-hexane:ethyl acetate=3:1) and recrystallizing it with n-hexane again (yield: 64%).

The results of the NMR analysis that was carried out in order to confirm that the compound that was manufactured by using the above process was formed are described below.

$^1$H-NMR (300 MHz, $CDCl_3$): δ7.63 to 7.67 (2H), 7.43 to 7.48 (4H), 6.85 to 6.89 (4H), 6.29 to 6.34 (2H), 6.21 to 6.22 (2H), 4.39 to 4.42 (2H), 4.19 to 4.23 (2H), 3.93 to 3.95 (2H), 2.62 to 2.99 (2H), 1.97 to 1.98 (2H), 1.78 to 1.85 (4H), 1.38 to 1.60 (2H), 1.02 to 1.05 (6H)

Synthetic Example 6-(2)

Synthesis of 5-norbornene-2,3-di(4-propoxy cinnamate)

5-norbornene-2,3-di(methanol) (15.4 g, and 0.1 mol) that was manufactured in Synthetic Example 2, the 4-propoxy cinnamic acid (53 g, 0.22 mol), and $Zr(OAc)_x(OH)_y$ (x+y=4) (Aldrich, 243 mg, 1 mmol) were put into the 250 ml two-neck flask, and dissolved in 500 ml of toluene. After the Dean-Stark distillation device was installed, the temperature was increased to 130° C., and the reflux was carried out. After the reaction was carried out for 48 hours, they were washed with 10% HCl aqueous solution, and extracted with a great amount of ethyl acetate. The obtained product was washed with the $NaHCO_3$ aqueous solution, dried with anhydrous $MgSO_4$, and filtered. In addition, the product was obtained by removing the solvent by using the rotary evaporator. The pure product was obtained by recrystallizing it with n-hexane again (yield: 45%).

Example 1

Polymerization of 5-norbornene-2,3-di(cinnamate)

17 g of 5-norbornene-2,3-di(cinnamate) (40 mmol) and 100 ml of toluene that was purified with the solvent were added to the 250 ml schlenk flask. 9 mg of $Pd(OAc)_2$ that was dissolved in 5 ml of dichloromethane and 77 mg of tricyclohexylphosphoniumtetrakis(pentafluorophenyl)borate were added to this flask as the catalyst, and reacted while being agitated for 18 hours at 90° C.

After the reaction for 18 hours, the reactants were diluted with a small amount of chlorobenzene, and added to an excessive amount of ethanol to obtain the white polymer precipitate. This precipitate was filtered by using the glass funnel, and the recovered polymer was dried in the vacuum oven 50° C. for 24 hours to obtain 11 g of the 5-norbornene-2,3-di(cinnamate) polymer.

(Mw=123,000, PDI=2.13, yield=65%).

Example 2

Polymerization of 5-norbornene-2,3-di(4-methoxy-cinnamate)

18 g of 5-norbornene-2,3-di(4-methoxy cinnamate) (40 mmol) and 100 ml of toluene that was purified with the solvent were added to the 250 ml schlenk flask. 9 mg of $Pd(OAc)_2$ that was dissolved in 5 ml of dichloromethane and 77 mg of tricyclohexylphosphoniumtetrakis(pentafluorophenyl)borate were added to this flask as the catalyst, and reacted while being agitated for 18 hours at 90° C.

After the reaction for 18 hours, the reactants were diluted with a small amount of chlorobenzene, and added to an excessive amount of ethanol to obtain the white polymer precipitate. This precipitate was filtered by using the glass funnel, and the recovered polymer was dried in the vacuum oven 50° C. for 24 hours to obtain 14.2 g of the 5-norbornene-2,3-di(4-methoxy cinnamate) polymer.

(Mw=110,000, PDI=2.27, yield=79%).

Example 3

Polymerization of 5-norbornene-2,3-di(4-ethoxy cinnamate)

20 g of 5-norbornene-2,3-di(4-ethoxy cinnamate) (40 mmol) and 100 ml of toluene that was purified with the solvent were added to the 250 ml schlenk flask. 9 mg of $Pd(OAc)_2$ that was dissolved in 5 ml of dichloromethane and 77 mg of tricyclohexylphosphoniumtetrakis(pentafluorophenyl)borate were added to this flask as the catalyst, and reacted while being agitated for 18 hours at 90° C.

After the reaction for 18 hours, the reactants were diluted with a small amount of chlorobenzene, and added to an excessive amount of ethanol to obtain the white polymer precipitate. This precipitate was filtered by using the glass funnel, and the recovered polymer was dried in the vacuum oven 50° C. for 24 hours to obtain 15.2 g of the 5-norbornene-2,3-di(4-ethoxy cinnamate) polymer.

(Mw=188,000, PDI=2.21, and yield=76%)

Example 4

Polymerization of 5-norbornene-2,3-di(4-propoxy cinnamate)

20 g of 5-norbornene-2,3-di(4-propoxy cinnamate) (38 mmol) and 100 ml of toluene that was purified with the solvent were added to the 250 ml schlenk flask. 8.5 mg of $Pd(OAc)_2$ that was dissolved in 5 ml of dichloromethane and 73 mg of tricyclohexylphosphoniumtetrakis(pentafluorophenyl)borate were added to this flask as the catalyst, and reacted while being agitated for 18 hours at 90° C.

After the reaction for 18 hours, the reactants were diluted with a small amount of chlorobenzene, and added to an excessive amount of ethanol to obtain the white polymer precipitate. This precipitate was filtered by using the glass funnel, and the recovered polymer was dried in the vacuum oven 50° C. for 24 hours to obtain 10 g of the 5-norbornene-2,3-di(4-propoxy cinnamate) polymer.

(Mw=84,000, PDI=1.96, and yield=50%).

Comparative Example 1

The polymer that included the repeating unit represented by the following Formula 7 was manufactured by using a known manufacturing method.

[Formula 7]

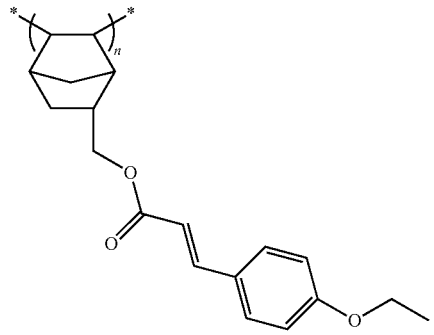

wherein n is 350.

(5-norbornene-2-ethoxy cinnamate polymer)

Experimental Example

Manufacturing of the Liquid Crystal Alignment Film

The polymers that were manufactured in Examples 1 to 4 and the polymer of Comparative Example 1 were dissolved in the c-pentanone solvent in a concentration of 5 wt %, and coated on the glass substrate by using a spin coating method so that the thickness after the drying was 80 nm. Next, it was heated in the oven at 120° C. for 2 min, such that the solvent in the coating film was removed, thus forming the coating film.

The exposure was carried out by using the high pressure mercury lamp in the intensity of 15 mW/cm² @365 nm as the light source, UV was irradiated onto the coating film by emitting the UV that was polarized in a direction that was vertical to a progress direction of the film by using the wire-grid polarizer manufactured by Moxtek, Co., Ltd., thereby manufacturing the liquid crystal alignment film.

Experimental Example 1

Photoreactive Speed Evaluation FT-IR Spectrum

In the process for manufacturing the liquid crystal alignment film using the polymers of Example 3 and Comparative Example 1, while the double bond peaks of 1640 cm⁻¹ and 980 cm⁻¹ of the cinnamate group were monitored in-situ through FT-IR in conjunction with the irradiation of light, the peak intensity according to the UV energy (J/cm²) was measured, and the result is illustrated in FIG. 1.

In addition, in the process for manufacturing the liquid crystal alignment film using Example 1, Example 2, Example 4 and Comparative Example 1, while the double bond peaks of 1640 cm⁻¹ and 980 cm⁻¹ of the cinnamate group were monitored in-situ through FT-IR in conjunction with the irradiation of light, the peak intensity according to the time (sec) was measured, and the result is illustrated in FIG. 2.

For reference, the UV energy (J/cm²)=UV intensity (W/cm²)*time (sec), and since the test was carried out by using the lamp that had the constant UV intensity (15 mW/cm²), the UV energy was proportional to the time. Accordingly, in FIGS. 1 and 2, there is no difference between the case of when the X axis was defined by the UV energy and the case of when the X axis was defined by the time in views of analysis of the results thereof.

Since the photoreaction speed R(p)=initial slope (initial slope on the IR graph)*[M] (concentration of cinnamate per unit volume), it could be seen that the polymers of Example 1 to Example 4 according to the present invention, in which the two cinnamate groups that were the photoreaction functional group were bonded to each other in the unit polymer, had the high initial slope on the IR graph and the largely improved photoreaction speed (R(p)) because of two times higher concentration item [M] value, as compared to the polymer of Comparative Example 1.

What is claimed is:

1. A norbornene monomer derivative that is represented by the following Formula 1:

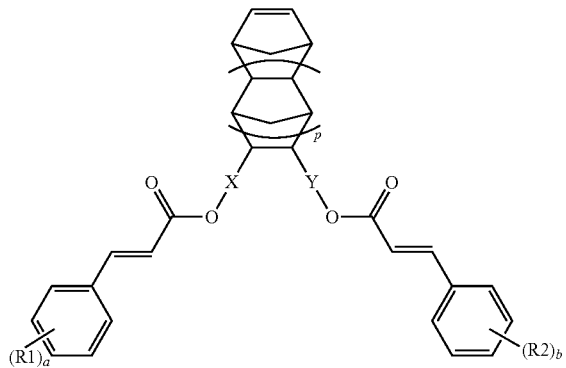

[Formula 1]

wherein P is an integer in the range of 0 to 4,

X and Y are the same as each other or different from each other, and substituted or unsubstituted $C_{1-20}$ alkylene, carbonyl, carboxy, or substituted or unsubstituted $C_{6-40}$ arylene, a and b are an integer in the range of 1 to 5, R1 and R2 are the same as each other or different from each other, and each selected from the group consisting of substituted or unsubstituted $C_{1-20}$ alkyl and substituted or unsubstituted $C_{1-20}$ alkoxy.

2. A method for manufacturing a norbornene monomer derivative according to claim 1, the method comprising the steps of:
  a) manufacturing exo-nadic anhydride by thermally rearranging endo-nadic anhydride;
  b) reducing the manufactured exo-nadic anhydride by using a reducing agent; and
  c) esterifying the manufactured product and an acidic cinnamate derivative.

* * * * *